(12) United States Patent
Brain

(10) Patent No.: US 9,974,912 B2
(45) Date of Patent: May 22, 2018

(54) ARTIFICIAL AIRWAY DEVICE

(75) Inventor: Archibald Ian Jeremy Brain, Mahe (SC)

(73) Assignee: Teleflex Life Sciences Unlimited Company, Hamilton (BM)

(*) Notice: Subject to any disclaimer, the term of this patent is extended or adjusted under 35 U.S.C. 154(b) by 329 days.

(21) Appl. No.: 13/876,146

(22) PCT Filed: Sep. 29, 2011

(86) PCT No.: PCT/GB2011/001421
§ 371 (c)(1),
(2), (4) Date: Jun. 11, 2013

(87) PCT Pub. No.: WO2012/042219
PCT Pub. Date: Apr. 5, 2012

(65) Prior Publication Data
US 2013/0247917 A1 Sep. 26, 2013

(30) Foreign Application Priority Data

Oct. 1, 2010 (GB) .................................... 1016562.9

(51) Int. Cl.
*A61M 16/00* (2006.01)
*A61M 16/04* (2006.01)

(52) U.S. Cl.
CPC .... *A61M 16/0463* (2013.01); *A61M 16/0409* (2014.02); *A61M 16/0415* (2014.02);
(Continued)

(58) Field of Classification Search
CPC .......... A61M 16/0463; A61M 16/0409; A61M 16/0434; A61M 16/0488; A61M 16/0493;
(Continued)

(56) References Cited

U.S. PATENT DOCUMENTS 2,099,127 A 11/1937 Leech
2,839,788 A 6/1958 Dembiak
(Continued)

FOREIGN PATENT DOCUMENTS

AU 647437 6/1991
CA 2067782 11/1989
(Continued)

OTHER PUBLICATIONS

International Search Report for PCT/GB2006/001913, dated Aug. 28, 2006.
(Continued)

*Primary Examiner* — Justine Yu
*Assistant Examiner* — Douglas Sul
(74) *Attorney, Agent, or Firm* — Knobbe, Martens, Olson & Bear, LLP

(57) ABSTRACT

The invention relates to an artificial airway device (1) to facilitate lung ventilation of a patient, comprising an airway tube (2) and a mask (3) carried at one end of the airway tube, the mask (3) having a distal end (4) and a proximal end (5) and a peripheral formation (6) capable of forming a seal around the circumference of the laryngeal inlet, the peripheral formation (6) surrounding a hollow interior space or lumen (7) of the (mask (3) and the bore of the airway tube (2) opening into the lumen (7) of the mask, the airway tube including support means (44) such that the cross sectional area of the bore is substantially maintained upon application of pressure by the patient's teeth, while allowing local deformation of the tube at the point of tooth contact.

2 Claims, 8 Drawing Sheets

(52) U.S. Cl.
CPC .... *A61M 16/0434* (2013.01); *A61M 16/0488* (2013.01); *A61M 16/0493* (2014.02)

(58) Field of Classification Search
CPC .......... A61M 25/0013; A61M 25/0051; A61M 25/0052; A61M 25/0138
USPC ............ 128/200.26, 202.27, 206.29, 207.14, 128/207.17
See application file for complete search history.

(56) References Cited

U.S. PATENT DOCUMENTS

| | | | |
|---|---|---|---|
| 2,862,498 A | 12/1958 | Weekes | |
| 3,529,596 A | 9/1970 | Garner | |
| 3,554,673 A | 1/1971 | Schwartz et al. | |
| 3,576,187 A * | 4/1971 | Oddera | A61M 16/0488 128/207.14 |
| 3,683,908 A | 8/1972 | Michael et al. | |
| 3,794,036 A | 2/1974 | Carroll | |
| 3,931,822 A | 1/1976 | Marici | |
| 3,948,273 A | 4/1976 | Sanders | |
| 4,056,104 A | 11/1977 | Jaffe | |
| 4,067,329 A | 1/1978 | Winicki et al. | |
| 4,104,357 A | 8/1978 | Blair | |
| 4,116,201 A | 9/1978 | Shah | |
| 4,134,407 A | 1/1979 | Elam | |
| 4,159,722 A | 7/1979 | Walker | |
| 4,166,467 A | 9/1979 | Abramson | |
| 4,178,938 A | 12/1979 | Au et al. | |
| 4,178,940 A | 12/1979 | Au et al. | |
| 4,231,365 A | 11/1980 | Scarberry | |
| 4,256,099 A | 3/1981 | Dryden | |
| 4,285,340 A | 8/1981 | Gezari et al. | |
| 4,338,930 A | 7/1982 | Williams | |
| 4,351,330 A | 9/1982 | Scarberry | |
| 4,363,320 A * | 12/1982 | Kossove | 128/207.14 |
| 4,446,864 A | 5/1984 | Watson et al. | |
| 4,471,775 A | 9/1984 | Clair et al. | |
| 4,501,273 A | 2/1985 | McGinnis | |
| 4,509,514 A | 4/1985 | Brain et al. | |
| 4,510,273 A | 4/1985 | Miura et al. | |
| 4,526,196 A | 7/1985 | Pistillo | |
| 4,553,540 A | 11/1985 | Straith | |
| 4,583,917 A | 4/1986 | Shah | |
| 4,630,606 A | 12/1986 | Weerda et al. | |
| 4,689,041 A | 8/1987 | Corday et al. | |
| 4,700,700 A | 10/1987 | Eliachar | |
| 4,770,170 A | 9/1988 | Sato et al. | |
| 4,793,327 A | 12/1988 | Frankel | |
| 4,798,597 A | 1/1989 | Vaillancourt | |
| 4,825,862 A | 5/1989 | Sato et al. | |
| 4,832,020 A | 5/1989 | Augustine | |
| 4,850,349 A | 7/1989 | Farahany | |
| 4,856,510 A | 8/1989 | Kowalewski et al. | |
| 4,872,483 A | 10/1989 | Shah | |
| 4,896,667 A | 1/1990 | Magnuson et al. | |
| 4,924,862 A | 5/1990 | Levinson | |
| 4,953,547 A | 9/1990 | Poole, Jr. | |
| 4,972,963 A | 11/1990 | Guarriello et al. | |
| 4,981,470 A | 1/1991 | Bombeck, IV | |
| 4,995,388 A | 2/1991 | Brain et al. | |
| 5,038,766 A | 8/1991 | Parker | |
| 5,042,469 A | 8/1991 | Augustine | |
| 5,042,476 A | 8/1991 | Smith | |
| 5,060,647 A | 10/1991 | Alessi | |
| 5,067,496 A | 11/1991 | Eisele | |
| 5,113,875 A | 5/1992 | Bennett | |
| 5,174,283 A | 12/1992 | Parker | |
| 5,203,320 A | 4/1993 | Augustine | |
| 5,218,970 A | 6/1993 | Turnbull et al. | |
| 5,235,973 A | 8/1993 | Levinson | |
| 5,241,325 A | 8/1993 | Nguyen et al. | |
| 5,241,956 A | 9/1993 | Brain et al. | |
| 5,249,571 A | 10/1993 | Brain et al. | |
| 5,273,537 A | 12/1993 | Haskvitz et al. | |
| 5,277,178 A | 1/1994 | DinQley et al. | |
| 5,282,464 A | 2/1994 | Brain et al. | |
| 5,297,547 A | 3/1994 | Brain et al. | |
| 5,303,697 A | 4/1994 | Brain et al. | |
| 5,305,743 A | 4/1994 | Brain | |
| 5,311,861 A | 5/1994 | Miller et al. | |
| 5,318,017 A | 6/1994 | Ellison | |
| 5,331,967 A | 7/1994 | Akerson et al. | |
| 5,339,805 A | 8/1994 | Parker | |
| 5,339,808 A | 8/1994 | Don Michael | |
| 5,355,879 A | 10/1994 | Brain et al. | |
| 5,361,753 A | 11/1994 | Pothmann et al. | |
| 5,391,248 A | 2/1995 | Brain et al. | |
| 5,400,771 A | 3/1995 | Pirak et al. | |
| 5,421,325 A | 6/1995 | Cinberg et al. | |
| 5,438,982 A | 8/1995 | Macintyre | |
| 5,443,063 A | 8/1995 | Greenberg | |
| 5,452,715 A | 9/1995 | Boussignac et al. | |
| 5,459,700 A | 10/1995 | Jacobs | |
| 5,487,383 A | 1/1996 | Levinson | |
| 5,529,582 A | 6/1996 | Fukuhara et al. | |
| 5,546,935 A | 8/1996 | Champeau | |
| 5,546,936 A | 8/1996 | Virag et al. | |
| 5,551,420 A | 9/1996 | Lurie et al. | |
| 5,554,673 A | 9/1996 | Shah | |
| 5,569,219 A | 10/1996 | Hakki et al. | |
| 5,577,693 A | 11/1996 | Corn | |
| 5,582,167 A | 12/1996 | Joseph | |
| 5,584,290 A | 12/1996 | Brain et al. | |
| 5,590,643 A * | 1/1997 | Flam | 128/200.26 |
| 5,599,301 A | 2/1997 | Jacobs et al. | |
| 5,623,921 A | 4/1997 | Kinsinger et al. | |
| 5,623,924 A | 4/1997 | Lindenman et al. | |
| 5,626,151 A | 5/1997 | Linden | |
| 5,632,271 A | 5/1997 | Brain et al. | |
| RE35,531 E | 6/1997 | Callaghan et al. | |
| 5,653,229 A | 8/1997 | Greenberg | |
| 5,655,528 A | 8/1997 | Paqan et al. | |
| 5,682,880 A | 11/1997 | Brain et al. | |
| 5,692,498 A | 12/1997 | Lurie et al. | |
| 5,694,929 A | 12/1997 | Christopher | |
| 5,711,293 A | 1/1998 | Brain et al. | |
| 5,738,094 A | 4/1998 | Hottman | |
| 5,743,254 A | 4/1998 | Parker | |
| 5,743,258 A | 4/1998 | Sato et al. | |
| 5,746,202 A | 5/1998 | Paqan et al. | |
| 5,771,889 A | 6/1998 | Pagan et al. | |
| 5,778,872 A | 7/1998 | Fukunaga et al. | |
| 5,791,341 A | 8/1998 | Bullard | |
| 5,794,617 A | 8/1998 | Brunell et al. | |
| 5,816,240 A | 10/1998 | Komesaroff | |
| 5,819,723 A | 10/1998 | Joseph | |
| 5,832,916 A | 11/1998 | Lundberg et al. | |
| 5,850,832 A | 12/1998 | Chu | |
| 5,855,203 A | 1/1999 | Matter | |
| 5,856,510 A | 1/1999 | Meng et al. | |
| 5,860,418 A | 1/1999 | Lundberg et al. | |
| 5,862,801 A * | 1/1999 | Wells | A61M 16/0493 128/200.26 |
| 5,865,176 A | 2/1999 | O'Neil et al. | |
| 5,878,745 A | 3/1999 | Brain et al. | |
| 5,881,726 A | 3/1999 | Neame | |
| 5,893,891 A | 4/1999 | Zahedi et al. | |
| 5,896,858 A | 4/1999 | Brain | |
| 5,915,383 A | 6/1999 | Pagan | |
| 5,921,239 A | 7/1999 | McCall et al. | |
| 5,924,862 A | 7/1999 | White | |
| 5,937,860 A | 8/1999 | Cook | |
| 5,957,133 A | 9/1999 | Hart | |
| 5,976,075 A | 11/1999 | Beane et al. | |
| 5,979,445 A | 11/1999 | Neame et al. | |
| 5,983,891 A | 11/1999 | Fukunaga | |
| 5,983,896 A | 11/1999 | Fukunaqa et al. | |
| 5,983,897 A | 11/1999 | Pagan | |
| 5,988,167 A | 11/1999 | Kamen | |
| 5,996,582 A | 12/1999 | Turnbull | |
| 6,003,510 A | 12/1999 | Anunta | |
| 6,003,511 A | 12/1999 | Fukunaga et al. | |
| 6,003,514 A | 12/1999 | Pagan | |

(56) References Cited

U.S. PATENT DOCUMENTS

| | | |
|---|---|---|
| 6,012,452 A | 1/2000 | Pagan |
| 6,021,779 A | 2/2000 | Pagan |
| 6,050,264 A | 4/2000 | Greenfield |
| 6,062,219 A | 5/2000 | Lurie et al. |
| 6,070,581 A | 6/2000 | Augustine et al. |
| 6,079,409 A | 6/2000 | Brain et al. |
| D429,811 S | 8/2000 | Bermudez et al. |
| 6,095,144 A | 8/2000 | Pagan |
| 6,098,621 A | 8/2000 | Esnouf et al. |
| 6,110,143 A | 8/2000 | Kamen |
| 6,116,243 A | 9/2000 | Pagan |
| 6,119,695 A | 9/2000 | Augustine et al. |
| 6,131,571 A | 10/2000 | Lamootang et al. |
| 6,149,603 A | 11/2000 | Parker |
| 6,155,257 A | 12/2000 | Lurie et al. |
| 6,213,120 B1 | 4/2001 | Block et al. |
| 6,224,562 B1 | 5/2001 | Lurie et al. |
| 6,234,985 B1 | 5/2001 | Lurie et al. |
| 6,240,922 B1 | 6/2001 | Pagan |
| 6,251,093 B1 | 6/2001 | Valley et al. |
| 6,269,813 B1 | 8/2001 | Fitzgerald et al. |
| 6,315,739 B1 | 11/2001 | Merilainen et al. |
| 6,338,343 B1 | 1/2002 | Augustine et al. |
| 6,352,077 B1 | 3/2002 | Shah |
| 6,386,199 B1 | 5/2002 | Alfery |
| 6,390,093 B1 | 5/2002 | Mongeon |
| 6,422,239 B1 | 7/2002 | Cook |
| 6,427,686 B2 | 8/2002 | Augustine et al. |
| 6,439,232 B1 | 8/2002 | Brain |
| 6,450,164 B1 | 9/2002 | Banner et al. |
| 6,508,250 B1 | 1/2003 | Esnouf |
| 6,546,931 B2 | 4/2003 | Lin et al. |
| 6,631,720 B1 | 10/2003 | Brain et al. |
| 6,647,984 B1 | 11/2003 | O'Dea et al. |
| 6,651,666 B1 | 11/2003 | Owens |
| 6,705,318 B1 | 3/2004 | Brain |
| 6,766,801 B1 | 7/2004 | Wright |
| 6,955,645 B1 | 10/2005 | Zeitels |
| 7,004,169 B2 | 2/2006 | Brain et al. |
| 7,040,322 B2 | 5/2006 | Fortuna et al. |
| 7,051,096 B1 | 5/2006 | Krawiec et al. |
| 7,051,736 B2 | 5/2006 | Banner et al. |
| 7,096,868 B2 | 8/2006 | Tateo et al. |
| 7,097,802 B2 | 8/2006 | Brain et al. |
| 7,128,071 B2 | 10/2006 | Brain et al. |
| 7,134,431 B2 | 11/2006 | Brain et al. |
| 7,156,100 B1 | 1/2007 | Brain et al. |
| 7,159,589 B2 | 1/2007 | Brain |
| RE39,938 E | 12/2007 | Brain |
| 7,383,736 B2 | 6/2008 | Esnouf |
| 7,694,682 B2 | 4/2010 | Petersen et al. |
| 7,997,274 B2 | 8/2011 | Baska |
| 8,033,176 B2 | 10/2011 | Esnouf |
| 8,413,658 B2 * | 4/2013 | Williams .......... A61M 16/0488 128/200.26 |
| 9,078,559 B2 | 7/2015 | Tsunoda et al. |
| 2003/0000534 A1 | 1/2003 | Alfery |
| 2003/0037790 A1 | 2/2003 | Brain |
| 2003/0051734 A1 | 3/2003 | Brain |
| 2003/0101998 A1 | 6/2003 | Zecca et al. |
| 2003/0131845 A1 | 7/2003 | Lin |
| 2003/0168062 A1 | 9/2003 | Blythe et al. |
| 2003/0172925 A1 | 9/2003 | Zecca et al. |
| 2003/0172935 A1 | 9/2003 | Miller |
| 2004/0020491 A1 | 2/2004 | Fortuna |
| 2004/0089307 A1 | 5/2004 | Brain |
| 2005/0066975 A1 | 3/2005 | Brain |
| 2005/0081861 A1 | 4/2005 | Nasir |
| 2005/0090712 A1 | 4/2005 | Cubb |
| 2005/0133037 A1 * | 6/2005 | Russell .................. 128/207.15 |
| 2005/0139220 A1 | 6/2005 | Christopher |
| 2005/0178388 A1 | 8/2005 | Kuo |
| 2005/0199244 A1 | 9/2005 | Tateo et al. |
| 2005/0274383 A1 | 12/2005 | Brain |
| 2006/0124132 A1 | 6/2006 | Brain |
| 2006/0180156 A1 | 8/2006 | Baska |
| 2006/0201516 A1 | 9/2006 | Petersen et al. |
| 2006/0254596 A1 | 11/2006 | Brain |
| 2007/0089754 A1 | 4/2007 | Jones |
| 2007/0240722 A1 | 10/2007 | Kessler |
| 2008/0041392 A1 | 2/2008 | Cook |
| 2008/0142017 A1 | 6/2008 | Brain |
| 2008/0276936 A1 | 11/2008 | Cook |
| 2008/0308109 A1 * | 12/2008 | Brain ...................... 128/207.14 |
| 2009/0090356 A1 | 4/2009 | Cook |
| 2009/0133701 A1 | 5/2009 | Brain |
| 2009/0139524 A1 | 6/2009 | Esnouf |
| 2009/0145438 A1 | 6/2009 | Brain |
| 2010/0059061 A1 | 3/2010 | Brain |
| 2010/0089393 A1 | 4/2010 | Brain |
| 2010/0211140 A1 | 8/2010 | Barbut et al. |
| 2010/0242957 A1 | 9/2010 | Fortuna |
| 2011/0023890 A1 | 2/2011 | Baska |
| 2011/0220117 A1 | 9/2011 | Dubach |
| 2012/0085351 A1 | 4/2012 | Brain |
| 2012/0090609 A1 | 4/2012 | Dubach |
| 2012/0145161 A1 | 6/2012 | Brain |
| 2012/0174929 A1 | 7/2012 | Esnouf |
| 2012/0186510 A1 | 7/2012 | Esnouf |
| 2014/0034060 A1 | 2/2014 | Esnouf et al. |
| 2015/0209538 A1 * | 7/2015 | Hansen ............ A61M 16/0816 128/207.15 |

FOREIGN PATENT DOCUMENTS

| | | |
|---|---|---|
| CA | 2141167 | 1/1994 |
| CA | 2012750 | 8/1999 |
| CN | 1863568 A | 11/2006 |
| CN | 2882657 Y | 3/2007 |
| CN | 101057994 A | 10/2007 |
| CN | 201516220 U | 6/2010 |
| CN | 201719659 U | 1/2011 |
| CN | 102335478 A | 2/2012 |
| DE | 4447186 | 7/1996 |
| DE | 10042172 A1 | 4/2001 |
| EP | 0294200 A2 | 12/1988 |
| EP | 0294200 B1 | 12/1988 |
| EP | 0389272 A2 | 9/1990 |
| EP | 0402872 A1 | 12/1990 |
| EP | 0580385 A1 | 1/1994 |
| EP | 0712638 A1 | 5/1996 |
| EP | 0732116 A2 | 9/1996 |
| EP | 0796631 A2 | 9/1997 |
| EP | 0842672 A2 | 5/1998 |
| EP | 0845276 A2 | 6/1998 |
| EP | 0865798 A2 | 9/1998 |
| EP | 0922465 A2 | 6/1999 |
| EP | 0935971 A2 | 8/1999 |
| EP | 1119386 B1 | 8/2001 |
| EP | 1125595 A1 | 8/2001 |
| EP | 1 938 855 | 7/2008 |
| EP | 2 044 969 | 4/2009 |
| GB | 1529190 A | 10/1978 |
| GB | 2111394 A | 7/1983 |
| GB | 2205499 A | 12/1988 |
| GB | 2 298 580 | 9/1996 |
| GB | 2298797 A | 9/1996 |
| GB | 2317342 A | 3/1998 |
| GB | 2317830 A | 4/1998 |
| GB | 2318735 A | 5/1998 |
| GB | 2319478 A | 5/1998 |
| GB | 2321854 A | 8/1998 |
| GB | 2323289 A | 9/1998 |
| GB | 2323290 A | 9/1998 |
| GB | 2323291 A | 9/1998 |
| GB | 2323292 A | 9/1998 |
| GB | 2324737 A | 11/1998 |
| GB | 2334215 A | 8/1999 |
| GB | 2359996 A | 9/2001 |
| GB | 2371990 A | 8/2002 |
| GB | 2 404 863 | 2/2005 |
| GB | 2405588 A | 3/2005 |
| GB | 2 444 779 | 6/2008 |
| GB | 2 465 453 | 5/2010 |

(56) References Cited

FOREIGN PATENT DOCUMENTS

| | | |
|---|---|---|
| JP | 57-110261 | 7/1982 |
| JP | 03039169 A | 2/1991 |
| JP | 10118182 A | 5/1998 |
| JP | 10216233 A | 8/1998 |
| JP | 10263086 A | 10/1998 |
| JP | 10277156 A | 10/1998 |
| JP | 10314308 A | 12/1998 |
| JP | 10323391 A | 12/1998 |
| JP | 10328303 A | 12/1998 |
| JP | 11128349 A | 5/1999 |
| JP | 11192304 A | 7/1999 |
| JP | 11206885 A | 8/1999 |
| JP | 2000152995 A | 6/2000 |
| JP | 2003528701 A | 9/2003 |
| JP | 2007-514496 A | 6/2007 |
| JP | 2007-533337 A | 11/2007 |
| JP | 2008-136791 A | 6/2008 |
| TW | 200942206 A | 10/2009 |
| WO | WO9103207 A1 | 3/1991 |
| WO | WO9107201 A1 | 5/1991 |
| WO | WO9112845 A1 | 9/1991 |
| WO | WO9213587 A1 | 8/1992 |
| WO | WO 94/02191 | 2/1994 |
| WO | WO9402191 A1 | 2/1994 |
| WO | WO9533506 A1 | 12/1995 |
| WO | WO9712640 A1 | 4/1997 |
| WO | WO9712641 A1 | 4/1997 |
| WO | WO9816273 A1 | 4/1998 |
| WO | WO9850096 | 11/1998 |
| WO | WO9906093 A1 | 2/1999 |
| WO | WO 99/27840 | 6/1999 |
| WO | WO009189 A1 | 2/2000 |
| WO | WO0022985 A1 | 4/2000 |
| WO | WO0023135 A1 | 4/2000 |
| WO | WO0061212 A1 | 10/2000 |
| WO | WO0124860 | 4/2001 |
| WO | WO0174431 A2 | 10/2001 |
| WO | WO0232490 A2 | 4/2002 |
| WO | WO 2004/016308 | 2/2004 |
| WO | WO2004030527 A1 | 4/2004 |
| WO | WO 2004/089453 | 10/2004 |
| WO | WO 2005/011784 | 2/2005 |
| WO | WO2005011784 A1 | 2/2005 |
| WO | WO2005023350 A1 | 3/2005 |
| WO | WO 2005/046751 | 5/2005 |
| WO | WO 2005/058402 A1 | 6/2005 |
| WO | WO2006026237 A1 | 3/2006 |
| WO | WO2006125989 A1 | 11/2006 |
| WO | WO 2007071429 A2 * | 6/2007 ............ A61M 16/04 |
| WO | WO 2007/071429 A2 | 10/2007 |
| WO | WO 2008/001724 | 1/2008 |
| WO | WO 2009/026628 | 3/2009 |
| WO | WO 2010/060226 A1 | 6/2010 |
| WO | WO 2010/060227 | 6/2010 |
| WO | WO 2010/066001 | 6/2010 |

OTHER PUBLICATIONS

M.O. Abdelatti; "A Cuff Pressure Controller for Tracheal Tubes and Laryngeal Mask Airways" Anaesthesia, 1999, 54, pp. 981-986 (1999 Blackwell Science Ltd).
Jonathan L. Benumo, M.D.; "Laryngeal Mask Airway and the ASA Difficult Airway Algorithm" Medical Intelligence Article; Anesthesiology, V 84, No. 3, Mar. 1996 (686-99).
Jonathan L. Benumo, M.D.; "Management of the Difficult Adult Airway" With Special Emphasis on Awake Tracheal Intubation; Anesthesiology V 75, No. 6: 1087-1110, 1991.
Bernhard, et al.; "Adjustment of Intracuff Pressure to Prevent Aspiration"; Anesthesiology, vol. 50, No. 4, 363-366, Apr. 1979.
Bernhard, et al.; "Physical Characteristics of and Rates of Nitrous Oxide Diffusion into Tracheal Tube Cuffs" Anesthesiology, vol. 48, No. 6 Jun. 1978, 413-417.
A.I.J. Brain, et al.: "The Laryngeal Mask Airway" Anesthesia, 1985, vol. 40, pp. 356-361.

A.I.J. Brain, et al.: "The Laryngeal Mask Airway—A Possible New Solution to Airway Problems in the Emergency Situation" Archives of Emergency Medicine, 1984, vol. 1, p. 229-232.
A.I.J. Brain; "The Laryngeal Mask—A New Concept in Airway Management" British Journal of Anaesthesia, 1983, vol. 55, p. 801-805.
A.I.J. Brain, et al.: "A New Laryngeal Mask Prototype" Anaesthesia, 1995, vol. 50, pp. 42-48.
A.I.J. Brain; "Three Cases of Difficult Intubation Overcome by the Laryngeal Mask Airway"; Anaesthesia, 1985, vol. 40, pp. 353-355.
J. Brimacombe; "The Split Laryngeal Mask Airway" ; Royal Perth Hospital, Perth 6001 Western Australia; Correspondence p. 639.
P.M. Brodrick et al.; "The Laryngeal Mask Airway" ; Anaesthesia, 1989, vol. 44, pp. 238-241; The Association of Anaesthetists of Gt Britain and Ireland.
Burgard et al.; "The Effect of Laryngeal Mask Cuff Pressure on Postoperative Sore Throat Incidence" ; Journal of Clinical Anesthesia 8: 198-201, 1996 by Elsevier Science Inc.
Caplan, et al.; "Adverse Respiratory Events in Anesthesia: A Closed Claims Analysis"; Anesthesiology vol. 72, No. 5: 828-833, May 1990.
Donald E. Craven, MD; "Prevention of Hospital-Acquired Pneumonia: Meaning Effect in Ounces, Pounds, and Tons"; Annals of Internal Medicine, vol. 122, No. 3, Feb. 1, 1995, pp. 229-231.
"Cuff-Pressure-Control CDR 2000"; LogoMed, Klarenplatz 11, D-53578 Windhagen, pp. 1-4.
P.R.F. Davies et al.; "Laryngeal Mask Airway and Tracheal Tube Insertion by Unskilled Personnel"; The Lancet, vol. 336, p. 977-979.
DeMello et al.; "The Use of the Laryngeal Mask Airway in Primary Anaesthesia" Cambridge Military Hospital, Aldershot, Hants GU11 2AN; pp. 793-794.
Doyle et al.; "Intraoperative Awareness: A Continuing Clinical Problem"; Educational Synopses in Anesthesiology and Critical Care Medicine the Online Journal of Anesthesiology vol. 3 No. 6 Jun. 1996, pp. 1-8.
F. Engbers; "Practical Use of 'Diprifusor' Systems"; Anaesthesia, 1998, vol. 53, Supplement 1, pp. 28-34; Blackwell Science Ltd.
Eriksson et al.; "Functional Assessment of the Pharynx at Rest and During Swallowing in Partially Paralyzed Humans" Anesthesiology, vol. 87, No. 5, Nov. 1997, pp. 1035-1042.
J.B. Glen; "The Development of 'Diprifusor': A TCI System for Propofol" Anaesthesia, 1998, vol. 53, Supplement 1, pp. 13-21, Blackwell Science Ltd.
J.M. Gray et al.; "Development of the Technology for 'Diprifusor' TCI Systems"; Anaesthesia, 1998, vol. 53, Supplement 1, pp. 22-27, Blackwell Science Ltd.
M.L. Heath; "Endotracheal Intubation Through the Laryngeal Mask—Helpful When Laryngoscopy is Difficult or Dangerous"; European Journal of Anaesthesiology 1991, Supplement 4, pp. 41-45.
S. Hickey et al.; "Cardiovascular Response to Insertion of Brian's Laryngeal Mask"; Anaesthesia, 1990, vol. 45, pp. 629-633, The Association of Anaesthetists of Gt Britain and Ireland.
Inomata et al.; "Transient Bilateral Vocal Cord Paralysis after Insertion of a Laryngeal Mask Airway"; Anesthesiology, vol. 82, No. 3, Mar. 1995, pp. 787-788.
L. Jacobson et al.; "A Study of Intracuff Pressure Measurements, Trends and Behaviour in Patients During Prolonged Periods of Tracheal Intubation" British Journal of Anaesthesia (1981), vol. 53, pp. 97-101; Macmillan Publishers Ltd. 1981.
V. Kambic et al.; "Intubation Lesions of the Larynx"; British Journal of Anaesthesia (1978), vol. 50, pp. 587-590; Macmillan Journals Ltd. 1978.
A.Kapila et al.; "Intubating Laryngeal Mask Airway: A Preliminary Assessment of Performance"; British Journal of Anaesthesia 1995, vol. 75: pp. 228-229.
Carl-Eric Lindholm; "Prolonged Endotracheal Intubation" ; Iussu Societatis Anaesthesiologicae Scandinavica Edita Suppllementum XXXIII 1969 v. 33 pp. 29-46.
S. Majumder et al.; "Bilateral Lingual Nerve Injury Following the Use of the Laryngeal Mask Airway" ; Anaesthesia, 1998, vol. 53, pp. 184-186, 1998 Blackwell Science Ltd.

(56) References Cited

OTHER PUBLICATIONS

Todd Martin; "Patentability of Methods of Medical Treatment: A Comparative Study"; HeinOnLine—82 J. Pat. & Trademark Off. Soc'y 2000, pp. 381-423.

Merriam-Webster's Collegiate Dictionary Tenth Edition, Springfield, Mass, U.S.A. (Convex) p. 254 & (Saddle) p. 1029.

D.M. Miller; "A Pressure Regulator for the Cuff of a Tracheal Tube" Anaesthesia, 1992, vol. 47, pp. 594-596; 1992 The Association of Anaesthetists of Gt Britain and Ireland.

Muthuswamy et al.; "The Use of Fuzzy Integrals and Bispectral Analysis of the Electroencephalogram to Preddict Movement Under Anesthesia"; Ieee Transactions on Biomedical Engineering, vol. 46, No. 3, Mar. 1999, pp. 291-299.

K. Nagai et al.; "Unilateral Hypoglossal Nerve Paralysis Following the Use of the Laryngeal Mask Airway"; Anaesthesia, 1994, vol. 49, pp. 603-604; 1994 The Association of Anaesthetists of Gt Britain and Ireland.

Lars J. Kangas; "Neurometric Assessment of Adequacy of Intraoperative Anesthetic" Medical Technology Brief, Pacific Northwest National Laboratory, pp. 1-3.

Observations by a third party concerning the European Patent Application No. 99947765.6-2318, dated Jan. 18, 2005.

R.I. Patel et al.; "Tracheal Tube Cuff Pressure"; Anaesthesia, 1984, vol. 39, pp. 862-864; 1984 The Association of Anaesthetists of Gt Britain and Ireland.

Written Opinion of the International Searching Authority for Application No. PCT/GB2006/001913.

Pennant et al.; "Comparison of the Endotracheal Tube and Laryngeal Mask in Airway Management by Paramedical Personnel"; Dept of Anesthesiology, University of Texas Southwestern Medical School; Anesth Analg 1992, vol. 74, pp. 531-534.

Pippin et al.; "Long-Term Tracheal Intubation Practice in the United Kingdom"; Anaesthesia, 1983, vol. 38, pp. 791-795.

J.C. Raeder et al.; "Tracheal Tube Cuff Pressures" Anaesthesia, 1985, vol. 40, pp. 444-447; 1985 The Association of Anaesthetists of Gt Britain and Ireland.

Response to Complaint for matter No. 4b 0 440-05, *LMA Deutschland GmbH* vs. *AMBU (Deutschland) GmbH*, dated Feb. 10, 2006.

Rieger et al.; "Intracuff Pressures Do Not Predict Laryngopharyngeal Discomfort after Use of the Laryngeal Mask Airway"; Anesthesiology 1997, vol. 87, pp. 63-67; 1997 American Society of Anesthesiologists, Inc.

R D Seegobin et al.; "Endotracheal Cuff Pressure and Tracheal Mucosal Blood Flow: Endoscopic Study of Effects of Four Large Volume Cuffs"; British Medical Jornal, vol. 288, Mar. 31, 1984, pp. 965-968.

B.A. Willis et al.; "Tracheal Tube Cuff Pressure" Anaesthesia, 1988, vol. 43, pp. 312-314; The Association of Anaesthetists of Gt Britain and Ireland.

L. Worthington et al.; "Performance of Vaporizers in Circle Systems" British Journal of Anaesthesia 1995, vol. 75.

J. Michael Wynn, M.D.; "Tongue Cyanosis after Laryngeal Mask Airway Insertion" Anesthesiology, vol. 80, No. 6, Jun. 1994, p. 1403.

Brimacombe, Joseph R., "Laryngeal Mask Anesthesia" Second Edition, Saunders 2005.

"Anaesthetic and respiratory equipment—Supralaryngeal airways and connectors", International Standard Controlled, ISO 11712, ISO 2009.

Miller, Donald, "A Proposed Classification and Scoring System for Supraglottic Sealing Airways: A Brief Review", Anesth Analg 2004; 99:1553-9.

Benumof, Jonathan, "The Glottic Aperture Seal Airway. A New Ventilatory Device", Anesthesiology, V. 88, No. 5., May 1998, pp. 1219-1226.

McIntyre, John, "History of Anaesthesia" Oropharyngeal and nasopharyngeal airways: I (1880-1995), Can. J. Anaesth 1996, vol. 43, vol. 6, pp. 629-635.

Ishimura, et al., "Impossible Insertion of the Laryngeal Mask Airway and Oropharyngeal Axes", Anesthesiology, V. 83, No. 4., Oct. 1995, pp. 867-869.

Verghese, et al., "Clinical assessment of the single use laryngeal mask airway—the LMA—Unique", British Journal of Anaesthesia 1998; vol. 80: 677-679.

* cited by examiner

ARTIFICIAL AIRWAY DEVICE

This application is the U.S. National Phase under 35 U.S.C. § 371 of International Application No. PCT/GB2011/001421, filed Sep. 29, 2011, which claims priority to the Great Britain Patent Application No. 1016562.9, filed Oct. 1, 2010.

The present invention relates to an artificial airway device.

Artificial airway devices such as the laryngeal mask airway device are well known devices useful for establishing airways in unconscious patients. In its most basic form a laryngeal mask airway device consists of an airway tube sand a mask carried at one end of the airway tube, the mask having a peripheral formation often known as a "cuff" which is capable of conforming to and of fitting within, the actual and potential space behind the larynx of the patient so as to form a seal around the laryngeal inlet. The cuff can be inflatable, and in most variants it surrounds a hollow interior space or lumen of the mask, the at least one airway tube opening into the lumen, U.S. Pat. No. 4,509,514 is one of the many publications that describe laryngeal mask airway devices such as this. Such devices have been in use for many years and offer an alternative to the older, even better known endotracheal tube. For at least seventy years, endotracheal tubes comprising a long slender tube with an inflatable balloon disposed at the tube's distal end have been used for establishing airways in unconscious patients. In operation, the endotracheal tube's distal end is inserted through the mouth of the patient, past the patient's trachea. Once so positioned, the balloon is inflated so as to form a seal with the interior lining of the trachea. After this seal is established, positive pressure may be applied to the tube's proximal end to ventilate the patient's lungs. Also, the seal between the balloon and the inner lining of the trachea protects the lungs from aspiration (e.g., the seal prevents material regurgitated from the stomach from being aspirated into the patient's lungs).

In contrast to the endotracheal tube, it is relatively easy to insert a laryngeal mask airway device into a patient and thereby establish an airway. Also, the laryngeal mask airway device is a "forgiving" device in that even if it is inserted improperly, it still tends to establish an airway. Accordingly, the laryngeal mask airway device is often thought of as a "life saving" device. Also, the laryngeal mask airway device may be inserted with only relatively minor manipulation of the patient's head, neck and jaw. Further, the laryngeal mask airway device provides ventilation of the patient's lungs without requiring contact with the sensitive inner lining of the trachea and the size of the airway established is typically significantly larger than the size of the airway established with an endotracheal tube. Also, the laryngeal mask airway device does not interfere with coughing to the same extent as endotracheal tubes. Largely due to these advantages, the laryngeal mask airway device has enjoyed increasing popularity in recent years.

U.S. Pat. Nos. 5,303,697 and 6,079,409 describe examples of prior art devices that may be referred to as "intubating laryngeal mask airway devices." The intubating device has the added advantage that it is useful for facilitating insertion of an endotracheal tube. After an intubating laryngeal mask airway device has been located in the patient, the device can act as a guide for a subsequently inserted endotracheal tube. Use of the laryngeal mask airway device in this fashion facilitates what is commonly known as "blind insertion" of the endotracheal tube. Only minor movements of the patient's head, neck and jaw are required to insert the intubating laryngeal mask airway device, and once the device has been located in the patient, the endotracheal tube may be inserted with virtually no additional movements of the patient. This stands in contrast to the relatively large motions, of the patient's head, neck and jaw that would be required if the endotracheal tube were inserted without the assistance of the intubating laryngeal mask airway device. Furthermore, these devices permit single-handed insertion from any user position without moving the head and neck of the patient from a neutral position, and can also be put in place without inserting fingers in the patient's mouth. Finally, it is believed that they are unique in being devices which are airway devices in their own right, enabling ventilatory control and patient oxygenation to be continuous during intubation attempts, thereby lessening the likelihood of desaturation.

Artificial airway devices of the character indicated are exemplified by the disclosures of U.S. Pat. No. 4,509,514; U.S. Pat. No. 5,249,571; U.S. Pat. No. 5,282,464; U.S. Pat. No. 5,297,547; U.S. Pat. No. 5,303,697; and by the disclosure of UK Patent 2,205.499.

Furthermore, devices with additional provision for gastric-discharge drainage are exemplified by EP 0 794 807; U.S. Pat. No. 4,995,388 (FIGS. 7 to 10); U.S. Pat. No. 5,241,956; and U.S. Pat. No. 5,355,879 and commonly known as gastro-laryngeal masks. These masks make provision for airway assurance to the patient who is at risk from vomiting or regurgitation of stomach contents whilst unconscious. From a reading of these prior art documents it will be appreciated that gastro-laryngeal masks present numerous and often conflicting requirements of design and manufacture to achieve designs that do not sacrifice any of the benefits of the more simpler designs described above.

Thus, in general, laryngeal mask airway devices aim to provide an airway tube of such cross-section as to assure more than ample ventilation of the lungs. Designs with provision for gastric drainage have been characterized by relatively complex internal connections and cross-sections calculated to serve in difficult situations where substantial solids could be present in a gastric discharge. As a result, the provision of a gastric discharge opening at the distal end of the mask applicable for direct service of the hypopharynx has resulted in a tendency for such masks to become bulky and unduly stiff, thus making for difficulty in properly inserting the mask. Undue bulk and stiffness run contrary to the requirement for distal flexibility for tracking the posterior curvature of the patient's anatomy on insertion, in such manner as to reliably avoid traumatic encounter. Moreover, manufacturing is made much more difficult and costly and the risks of device failure may be increased.

Problems such as these can be especially acute in devices formed from relatively rigid materials, like PVC, as opposed to the more traditional Liquid Silicon Rubber (LSR). In general, devices formed from materials such as PVC are attractive because they are cheaper to make, and can be offered economically as "single-use" devices. However, there are material differences in PVC and PVC adhesives, such as increased durometer hardness as compared to LSR, which affect how devices perform in use. For example, it has been observed that for a given volume of air, an LSR cuff will expand to a larger size than a comparable PVC cuff. This superior elasticity allows the LSR cuff to provide an anatomically superior seal with reduced mucosal pressure. To close the performance gap, the PVC cuff must be of reduced wall thickness. However, a PVC cuff of reduced wall thickness, deflated and prepared for insertion, will suffer from poor flexural response as the transfer of insertion force through the airway tube to cuff distal tip cannot be adequately absorbed. The cuff assembly must deflate to a thickness that preserves flexural performance i.e. resists epiglottic downfolding, but inflate so that a cuff wall thickness of less than or equal to 0.4 mm creates a satisfactory seal. And where mask backplates are formed from PVC, as well as cuffs, the fact that the increased durometer hardness of PVC is inversely proportional to flexural performance (hysteresis) means that the flexural performance of the device in terms of reaction, response and recovery on deformation is inferior to a compatable LSR device.

A problem experienced in the early days of the laryngeal mask was crushing and even puncture of the airway tube due to biting or abrasion by the patient's teeth. It will be remembered that the airway tube passes out through the patient's mouth between the teeth, usually in line with the incisors. This problem was addressed by the present inventor by providing an airway tube of flattened as opposed to circular section. Such an airway tube is illustrated in the drawings accompanying this application. A flattened section tube is less likely to contact the patient's teeth because it requires less clearance between the teeth and can be made to provide the same or a greater cross-sectional area for gas flow as a circular section tube.

A further expedient devised by the present inventor to prevent crushing and puncturing is the bite block. Bite blocks are now commonly used in laryngeal masks of all types. A bite block is a part of the device that is disposed to sit between the patient's teeth when the device is in place that is designed to be resistant to crushing and puncturing by the teeth. A bite block can be made by increasing the thickness of the wall of the airway tube, by forming the relevant section of the tube from a harder material, and by adding a reinforcement inside and or outside of the material of the airway tube. Although all of these expedients help prevent crushing and puncturing of the tube, they also to a greater or lesser extent increase the likelihood of damage to a patient's teeth by the device, particularly the airway tube, which can be particularly traumatic to a patient. It is an object of the present invention to seek to mitigate problems such as this.

According to the invention there is provided an artificial airway device to facilitate lung ventilation of a patient, comprising an airway tube and a mask carried at one end of the airway tube, the mask having a distal end and a proximal end and a peripheral formation capable of forming a seal around the circumference of the laryngeal inlet, the peripheral formation surrounding a hollow interior space or lumen of the mask and the bore of the airway tube opening into the lumen of the mask, the airway tube including support means such that the cross sectional area of the bore is substantially maintained upon application of pressure by the patient's teeth, whilst allowing local deformation of the tube at the point of tooth contact. In this way, the invention provides a device that has an airway tube that is resistant to crushing and puncture whilst also guarding against damage to a patient's teeth.

The support means may comprise an insert within the airway tube. The insert may comprise a wall disposed to contact and support the airway tube, the wall including a cut away portion disposed at a point that in use will be in line with the direction of biting of the patient's teeth.

As an alternative, the support means may comprise an external sleeve of the airway tube as shown in FIG. 8. The sleeve 54 may comprise a wall disposed to contact and support the airway tube, the wall including a cut away portion 54e disposed at a point that in use will be in line with the direction of biting of the patient's teeth.

The peripheral formation may be inflatable, such as for example an inflatable cuff.

It is preferred that the mask describes a substantially convex curve, from the proximal to distal end. It is further preferred that the mask body comprises a plate, the plate having a dorsal side and a ventral side, the dorsal side being substantially smooth and having a convex curvature across its width. It is also preferred that the dorsal surface of the airway tube corresponds in curvature to the curvature across the width of the plate. All of these expedients assist in making insertion of the mask easier.

The airway tube preferably comprises a relatively more rigid material than the mask body. Both the airway tube and the mask body preferably comprise a plastics material.

The invention will further be described by way of example and with reference to the following drawings, in which, FIG. 1 is an underplan, or ventral view of a device according to the invention;

Figure 1:
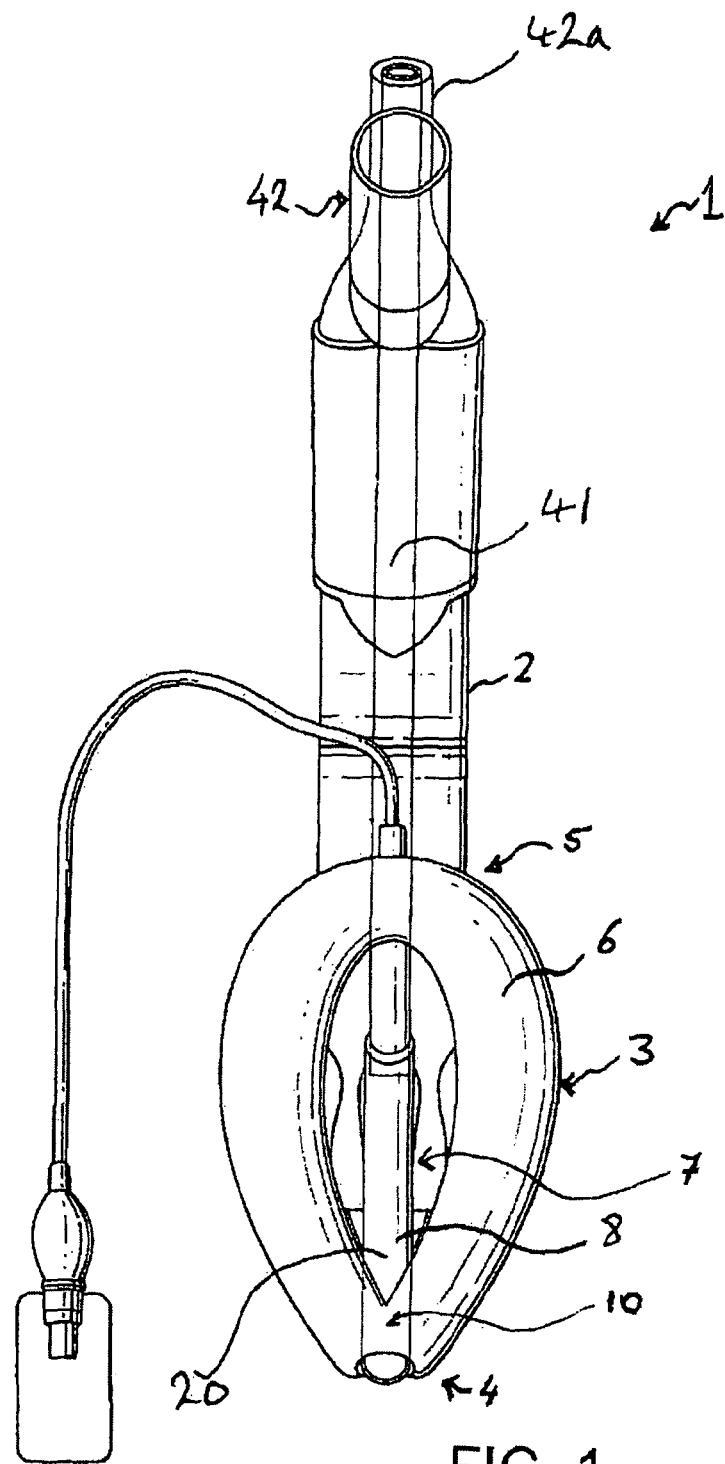

Referring now to the drawings, there is illustrated an artificial airway device 1 to facilitate lung ventilation of a patient, comprising an airway tube 2 and a mask 3 carried at one end of the airway tube, the mask 3 having a distal end 4 and a proximal end 5 and a peripheral formation 6 capable of forming a seal around the circumference of the laryngeal inlet, the peripheral formation 6 surrounding a hollow interior space or lumen 7 of the mask 3 and the bore of the airway tube 2 opening into the lumen 7 of the mask, the airway tube including support means 44 such that the cross sectional area of the bore is substantially maintained upon application of pressure by the patient's teeth, whilst allowing local deformation of the tube at the point of tooth contact.

As can be seen from the drawings, the device 1, in terms of overall appearance is somewhat similar to prior art devices, in that it consists of the basic parts which make up most if not all laryngeal mask airway devices, i.e. an airway tube 2 and mask 3. The mask 3 includes two components, a body part 11 often referred to as a backplate (shown in FIGS. 6 and 7), and a peripheral formation 6 which here takes the form of an inflatable cuff with an inflation line 12.

Figure 6:
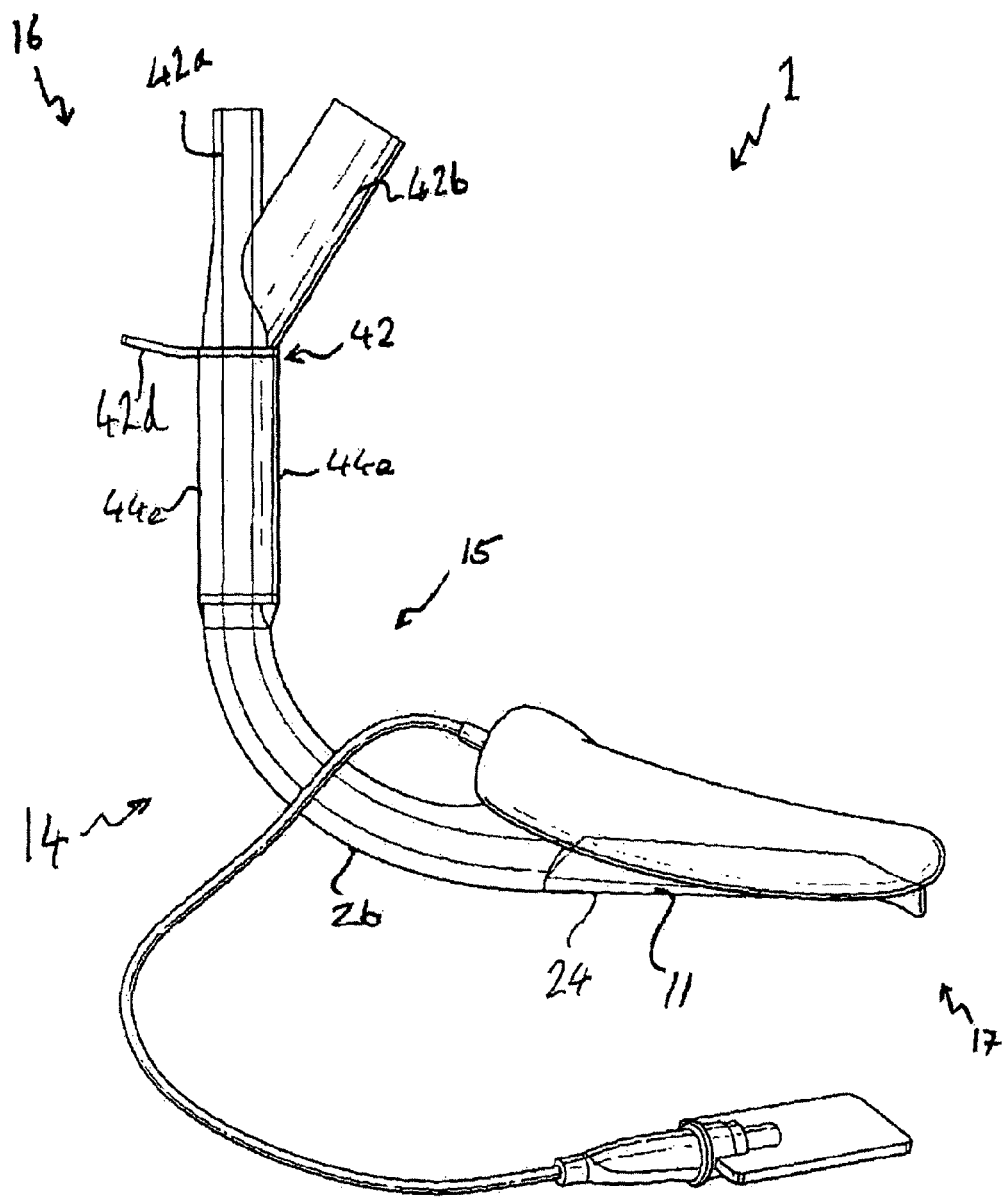
FIG. 6 is a side view of the device of FIG. 1.
Figure 7:
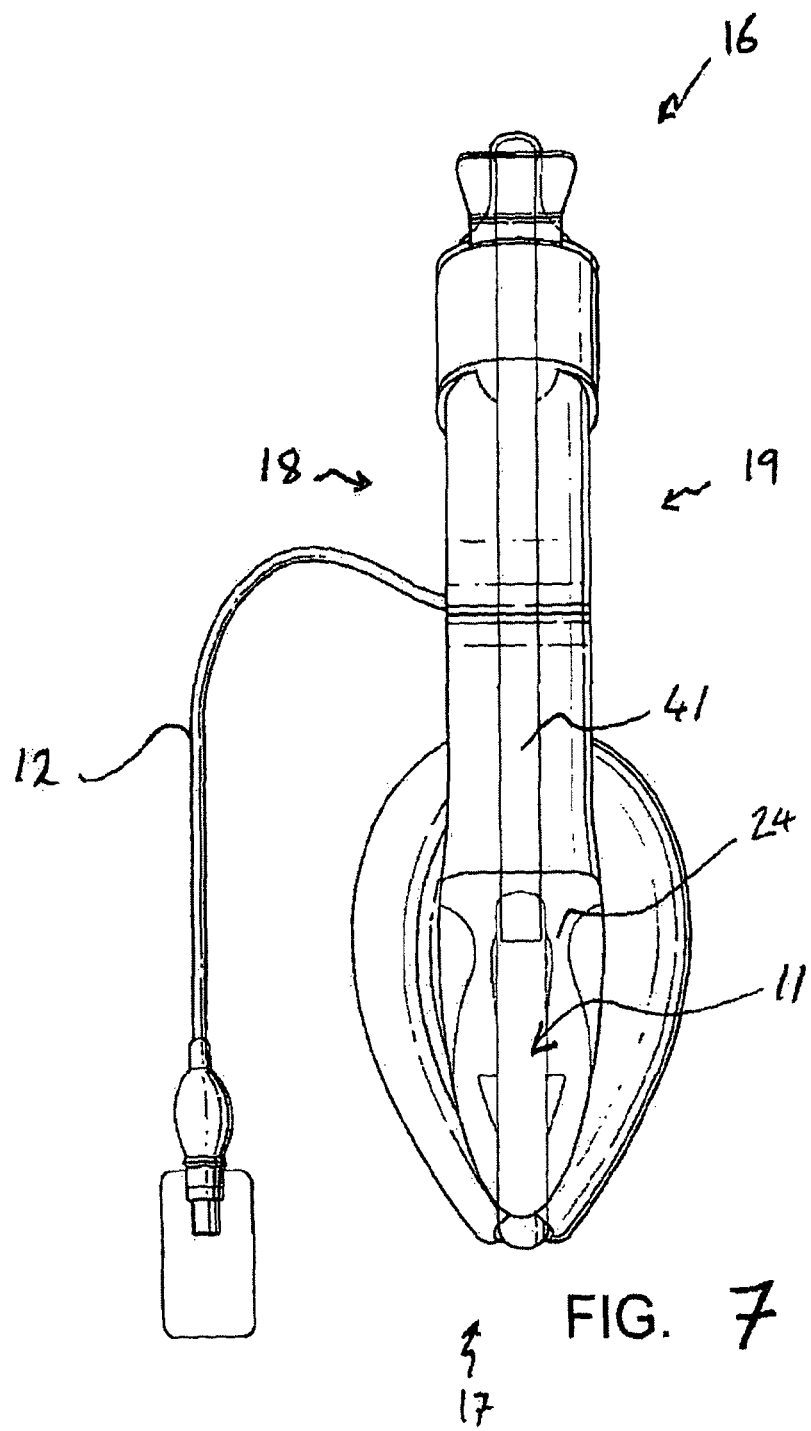
FIG. 7 is a plan, or dorsal view of the device of FIG. 1.
Figure 8:
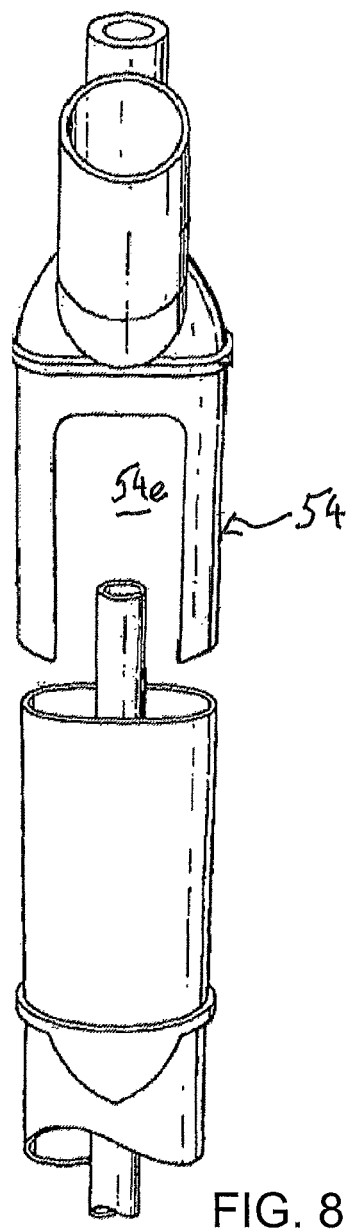
FIG. 8 is an exploded view of a part of an alternative embodiment of the device of FIG. 1.

For the purposes of description it is convenient to assign reference names to areas of the device 1 (as opposed to its constituent parts) and accordingly with reference to FIGS. 6 and 7, the device 1 has a dorsal side 14, a ventral side 15, a proximal end 16 (in a sense that this is the end nearest the user rather than the patient) a distal end 17 and right and left sides 18 and 19.

Referring firstly to the airway tube 2, in the illustrated embodiment the tube 2 comprises a relatively rigid PVC material such as a shore 90 A Colorite PVC moulded into an appropriately anatomically shaped curve. The tube 2 has some flexibility such that if it is bent it will return to its original shape. Although it is resiliently deformable in this way, it is also sufficiently rigid to enable it to assist in insertion of the device 1 into a patient acting as a handle and guide for positioning the mask. The airway tube 2 does not have a circular cross-section as in many prior devices, but instead is compressed in the dorsal/ventral direction which assists in correct insertion of the device 1, helps prevent kinking, and assists in comfortable positioning for the patient as the shape generally mimics the shape of the natural airway. In this embodiment each side 18, 19 of the airway tube 2 also includes a groove or channel 20 extending for most of the tube's length from the proximal to distal ends. These grooves 20 further assist in preventing crushing or kinking of the airway tube 2. Internally the grooves 20 form ridges along the inner surfaces of the sides 18 and 19, but this not essential to their operation.

Figure 2:
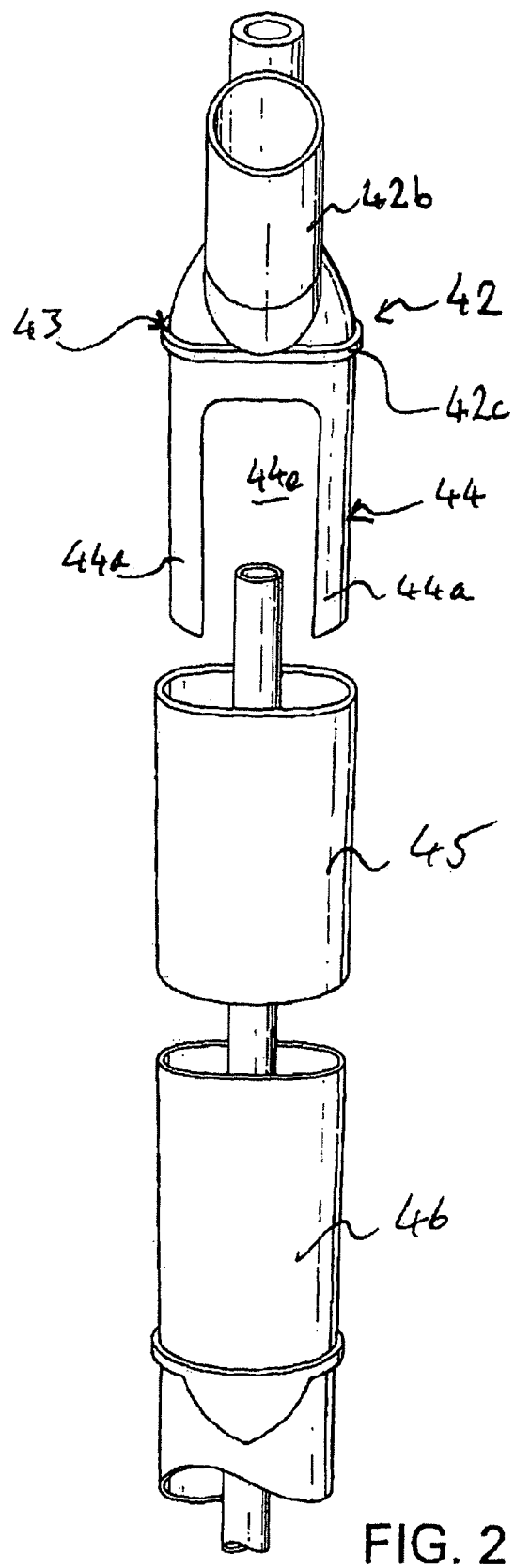
FIG. 2 is an exploded view of a part of the device of FIG. 1.
Figure 3:
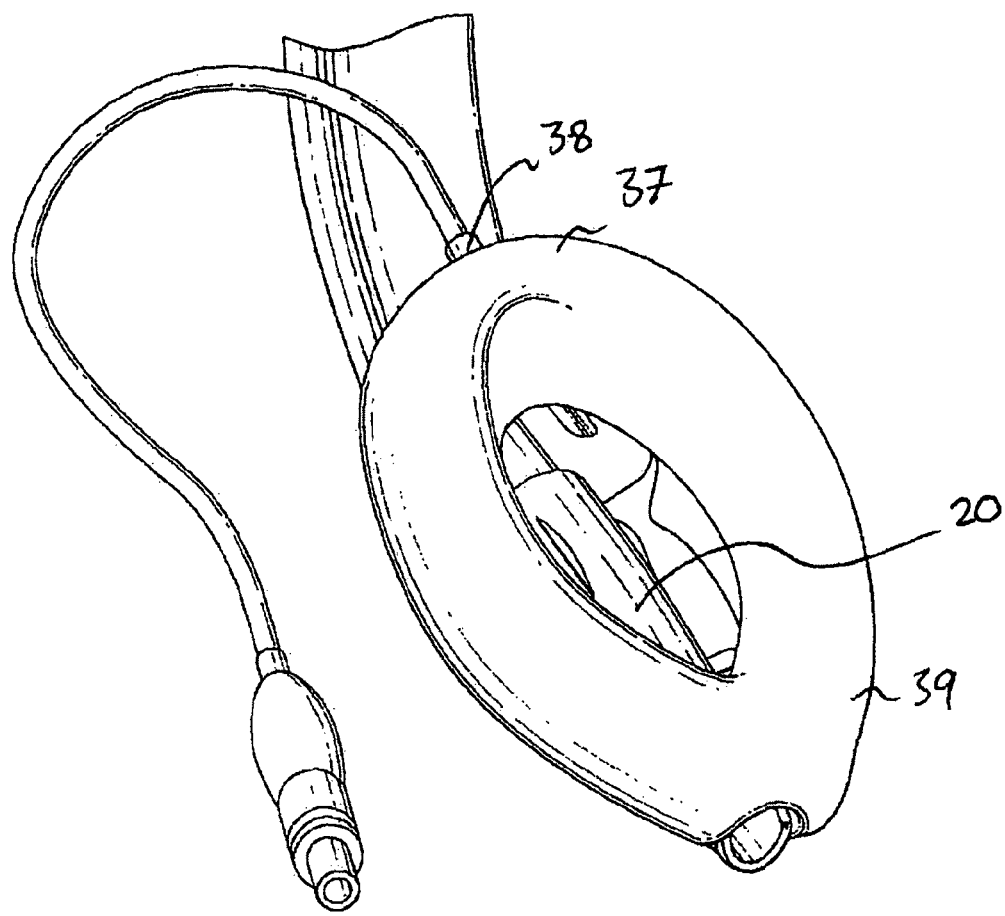
FIG. 3 is a perspective ventral view of the mask of the device of FIG. 1.
Figure 4:
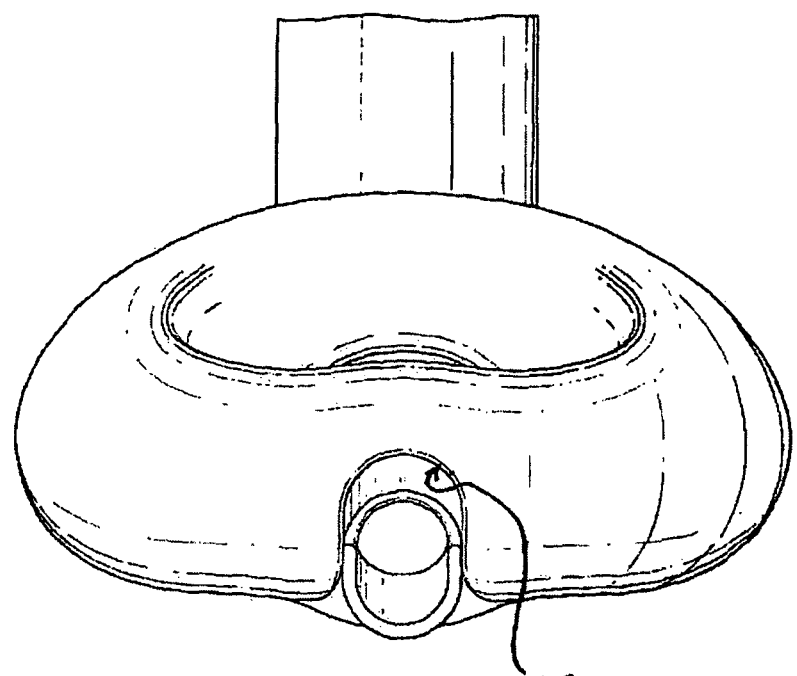
FIG. 4 is a front end view of the mask shown in FIG. 3 in a first position.

A further feature of the airway tube 2 is oesophageal drain tube 41. This drain tube 41 is located within airway tube 2, extending centrally through it from the proximal end to the distal end, and in this embodiment it is disposed in contact with the inner surface of the dorsal wall 2b of the airway tube 2, and bounded on each side by raised, smooth walls (not shown) which form a shallow channel through which it runs. At the proximal end of the airway tube 2, the drain tube 41 exits the airway tube 2 via branch 42a of a bifurcated connector 42, to which a suction line may be attached. Bifurcated connector 42 also allows for connection of the airway tube to a gas supply via branch 42b. Here it is formed from a relatively rigid plastics material (when compared with the airway tube 2) to enable easy connection of air lines and suction. Referring to FIG. 2, connector 42 comprises a hollow somewhat flattened, conical connector body 43 defining an atrium having branches 42a and 42b extending from its narrower, proximal end. Conical body 43 includes a circumferential flange 42c from which extends tab 42d in a direction generally normal to the longitudinal axis of the connector.

Referring to FIG. 2, an insert section. 44 extends longitudinally from the distal end of the conical body 43, forming a bite block which supports the tube 2 against crushing or puncturing by the patient's teeth. The insert section 44 can be described as a tube, flattened in the dorsal to ventral direction and having two sections of wall removed leaving gaps 44e and "arms" 44a which extend distally long the tube 2. The insert section 44 corresponds in shape and dimension with the internal shape of the proximal end of the airway tube 2 such that it fits snugly inside it with curved arms 44a corresponding in profile to and thereby providing support and rigidity to the sides of the airway tube. As a result of the removed wall sections 44e the support for the parts of the airway tube 2 adjacent the removed sections is reduced. such that a relatively softer, deformable surface is provided, although overall support for the tube 2 remains. In particular, it will be appreciated that supporting the sides of the airway tube using correspondingly shaped arms 44a prevents crushing of the airway tube. A sleeve 45 of a soft and compliant material is bonded in place around the outside of the airway tube 2, covering the area into which the insert section 44 locates, and the thickness of the airway tube wall at this point can be reduced to accommodate this such that the overall thickness at this point 46 is not increased. Thus, it will be appreciated that this configuration provides a bite block that not only supports the airway tube 2 at a point where the patient's teeth are normally located when the device is in use but also guards against damage to the teeth by virtue of the less rigid parts. It will be appreciated that this form of connector can also be applied to airway devices that do not include an oesophageal drain.

Turning now to the mask 3, the mask 3 consists of two parts, a body part 11 often referred to as a back plate, and a peripheral cuff 6.

Figure 5:
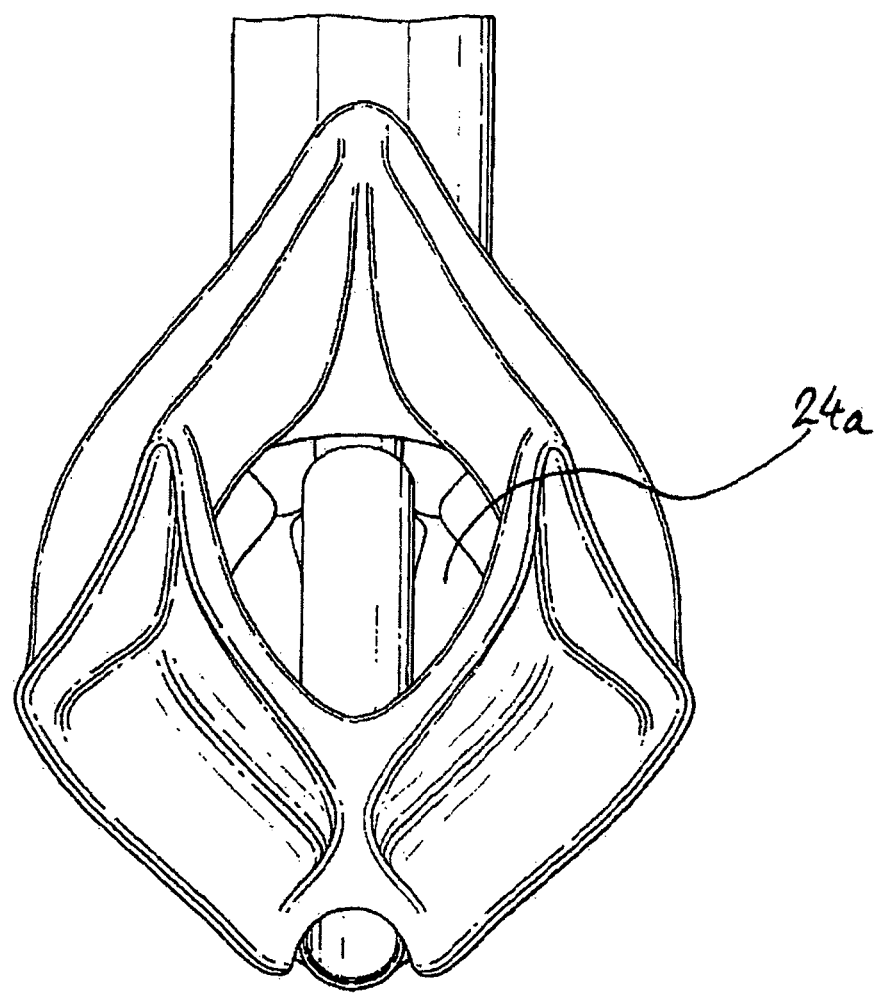
FIG. 5 is a front end view of the mask shown in FIG. 3 in a second, position.

The back plate 11 is formed by moulding from a shore 50 A Vythene PVC+PU. This material is substantially softer and more deformable than the material of airway tube 2. The back plate 11 comprises a generally oval moulding when viewed from the dorsal or ventral directions, having a smooth dorsal surface 24, and a formed ventral surface 24a (FIG. 5). The dorsal surface 24 has a convex curvature from one side to the other, corresponding to the curvature of the dorsal surface of the airway tube 2, and longitudinally, the dorsal surface 24 is also curved, having a curvature beginning at the joining portion 24b and extending with constant rate of curvature toward the distal tip. As a result the tip is ventrally biased relative to the distal end of the airway tube, in the assembled device 1, the extent of displacement of the distal tip being approximately 20 mm or 10 degrees, in order to produce a curvature in the mask that is suited to the anatomy of the patient. On insertion, this displacement of the tip assists the mask in "turning the corner" in the insertion path.

Backplate 11 includes an integrally moulded cylindrical drain tube 20 that extends from its proximal to distal ends. At the proximal end, the drain tube 11 is dimensioned such that it can be joined to the drain tube of the airway tube. At its distal, end, the wall of the drain tube 20 has a cut away portion 21, and a smooth, turned over edge.

The second part of the mask 3 is the peripheral cuff 6. The cuff 6 is in this embodiment blow moulded PVC and takes the form of a generally elliptical inflatable ring, a relatively deeper proximal end 37 with an inflation port 38 and a relatively shallower distal end tapering to a "wedge" profile 39. At the distal end the cuff is formed with a channel 22 in it is dorsal surface, the channel being of an open C shape that runs in a proximal to distal direction to the tip of the cuff. The cuff 6 is integrally formed in one piece. The wedge profile is provided such that the ratio of dorsal to ventral side surface areas favours the dorsal side. Thus, when deflated the distal end of the cuff 6 will curl with bias from dorsal to ventral side.

The cuff 6 is bonded to the backplate 11 such that the cut away section of the drain tube 20 extends over the channel 22 in the dorsal surface of the backplate 11, thereby forming a tube, part of the wall of which is formed by the backplate and part by the cuff 6. The tube terminates at or just before the distal extremity of the cuff, the smooth edge flaring to some extent in a dorsal direction.

In use, the deflated device 1 is inserted into a patient in the usual manner with devices of this type. As noted above, the relative rigidity of the airway tube 2 allows a user to grip it and use it to guide the device 1 into the patient whilst the relatively softer, more compliant material of the back plate means that the mask will more readily deform to negotiate the insertion path without causing damage to the anatomy, and will return to its optimum shape to ensure that a good seal is achieved at the furthest extent of insertion. The ventral displacement of the distal tip relative to the join between the back plate 11 and airway tube 2 further enhances ease of insertion, because the distal tip is thereby presented at the optimum angle to negotiate the "bend" in the insertion path. In devices formed from relatively rigid materials such as PVC, as opposed to the often used LSR these features are particularly important in easing insertion and providing for an enhanced seal. Once in place, the support 44 prevents crushing and puncturing of the airway tube 2 by the patient's teeth because the curved side walls of the airway tube 2 are supported by the correspondingly curved arms 44a of the support 44. However the tube 2 still guards against tooth damage because the cutaway gaps 44e allow some deformation of the surface of the tube 2.

The invention claimed is:

1. An artificial airway device to facilitate lung ventilation of a patient, comprising an airway tube having a bore, wherein the bore of the airway tube has a cross sectional area that is non-circular, and a mask carried at one end of the airway tube, the mask having a distal end and a proximal end and a peripheral formation capable of forming a seal around the circumference of the laryngeal inlet when in use, the peripheral formation surrounding a hollow interior space or lumen of the mask, the bore of the airway tube opening into the lumen of the mask, the airway tube including support means configured such that the cross sectional area of the bore is substantially maintained upon application of pressure by the patient's teeth when in use whilst allowing local deformation of the tube at the point of tooth contact with the device when in use, the support means comprising an insert within the airway tube, the insert including a wall disposed to contact and support the airway tube, the wall including a cut away portion on a dorsal portion and a ventral portion of the insert, the cut away portions configured to be disposed inside the tube at a point of tooth contact with the device when in use, the support means further including an external sleeve of the airway tube, the sleeve comprising a soft and compliant material bonded in place around the outside of the airway tube, covering the area into which the insert section locates.

2. The device according to claim 1, the peripheral formation comprising an inflatable cuff.

* * * * *